United States Patent
Wang et al.

(10) Patent No.: US 11,795,125 B2
(45) Date of Patent: Oct. 24, 2023

(54) INTEGRATED PROCESS FOR MAKING 1-CHLORO-3,3,3-TRIFLUOROPROPENE (HCFO-1233ZD) FROM A MIXTURE OF HIGH-BOILING FLUORINATED COMPONENTS

(71) Applicant: Honeywell International Inc., Charlotte, NC (US)

(72) Inventors: Haiyou Wang, Amherst, NY (US); Gustavo Cerri, Parsippany, NJ (US); Jinhua Yao, Shanghai (CN); Jennifer W. McClaine, Branchburg, NJ (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 18/083,238

(22) Filed: Dec. 16, 2022

(65) Prior Publication Data
US 2023/0234903 A1    Jul. 27, 2023

Related U.S. Application Data

(60) Provisional application No. 63/331,966, filed on Apr. 18, 2022.

(51) Int. Cl.
*C07C 17/23* (2006.01)
*C07C 17/383* (2006.01)
*B01J 27/132* (2006.01)

(52) U.S. Cl.
CPC .......... *C07C 17/23* (2013.01); *B01J 27/132* (2013.01); *C07C 17/383* (2013.01)

(58) Field of Classification Search
CPC ... C07C 17/25; C07C 21/18; C07C 2523/745; C07C 2527/132; C07C 17/23; C07C 17/383; B01J 27/132
See application file for complete search history.

(56) References Cited

U.S. PATENT DOCUMENTS

| 5,710,352 A | 1/1998 | Tung |
| 9,764,998 B2 | 9/2017 | Wang et al. |

(Continued)

FOREIGN PATENT DOCUMENTS

| CN | 112645793 A | 4/2021 |
| EP | 0931043 B1 | 8/2003 |

(Continued)

OTHER PUBLICATIONS

International Search Report and Written Opinion received for PCT Patent Application No. PCT/US2022/082446, dated May 12, 2023, 13 pages.

(Continued)

*Primary Examiner* — Jafar F Parsa
(74) *Attorney, Agent, or Firm* — Faegre Drinker Biddle & Reath LLP

(57) ABSTRACT

The present disclosure provides a method for conversion of a mixture of high-boiling fluorinated components comprising 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), 3-chloro-1,1,1,3-tetrafluoropropane (HCFC-244fa), their isomers, and combinations thereof, to 1-chloro-3,3,3-trifluoropropene (HCFO-1233zd). Heavy impurities, such as oligomers and other high boiling impurities, that are present may be purged during the process to prevent yield loss and reduction of catalyst efficacy.

20 Claims, 1 Drawing Sheet

(56) References Cited

U.S. PATENT DOCUMENTS

| | | | |
|---|---|---|---|
| 2016/0332936 A1* | 11/2016 | Wang | C07C 17/25 |
| 2019/0031583 A1* | 1/2019 | Okamoto | B01J 27/08 |
| 2021/0070680 A1 | 3/2021 | Ondrus et al. | |
| 2021/0130267 A1 | 5/2021 | Takahashi et al. | |

FOREIGN PATENT DOCUMENTS

| | | |
|---|---|---|
| JP | 5750917 B2 | 7/2015 |
| JP | 6015543 B2 | 10/2016 |
| WO | 2016/016625 A1 | 2/2016 |
| WO | 2022/083017 A1 | 4/2022 |

OTHER PUBLICATIONS

Zatsepina et al., "Processes for the Manufacture of 1-Chloro-3,3,3-Trifluoropropene," Fluorine Notes, vol. 2, No. 99, Apr. 2015, pp. 10.

* cited by examiner

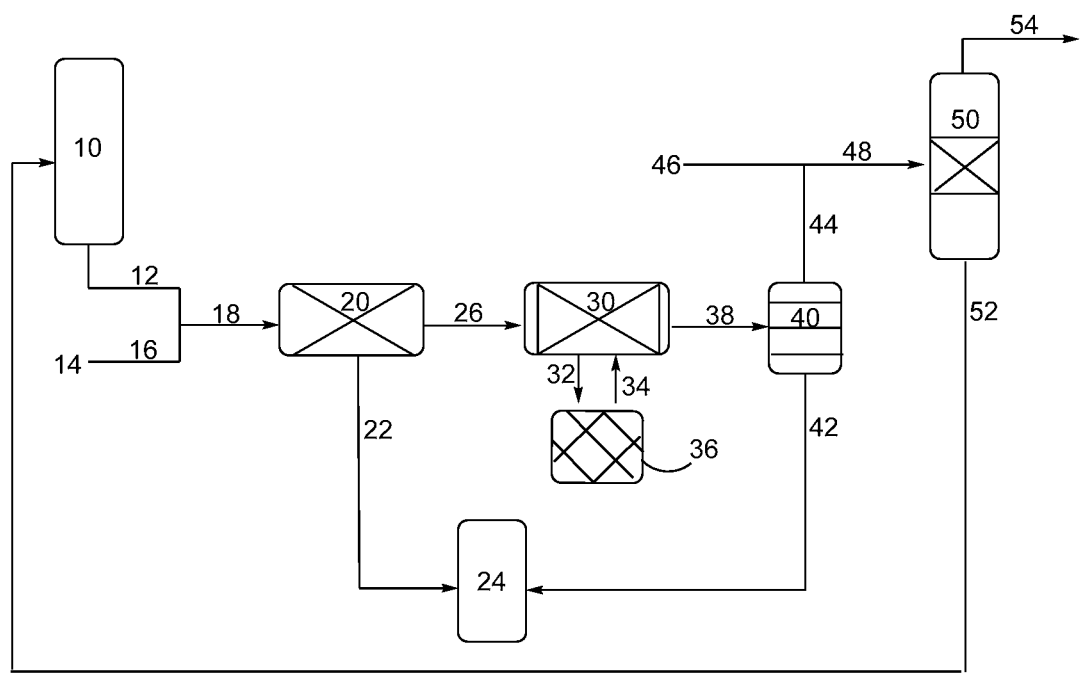

INTEGRATED PROCESS FOR MAKING 1-CHLORO-3,3,3-TRIFLUOROPROPENE (HCFO-1233ZD) FROM A MIXTURE OF HIGH-BOILING FLUORINATED COMPONENTS

CROSS-REFERENCE TO RELATED APPLICATION

This application claims priority to International Patent Application No. PCT/CN2022/073904, filed Jan. 26, 2022, and U.S. Provisional Patent Application No. 63/331,966, filed Apr. 18, 2022, both of which are herein incorporated by reference in their entireties.

FIELD

The present disclosure is related to an integrated process for making E-1-chloro-3,3,3-trifluoropropene (HCFO-1233zd(E)) and Z-1-chloro-3,3,3-trifluoropropene (HCFO-1233zd(Z)) from a mixture of high-boiling fluorinated components.

BACKGROUND

Chlorofluorocarbons (CFCs) like trichlorofluoromethane and dichlorodifluoromethane have been used as refrigerants, blowing agents and diluents for gaseous sterilization. In recent years, there has been widespread concern that certain chlorofluorocarbons might be detrimental to the Earth's ozone layer. As a result, there is a worldwide effort to use halocarbons which contain fewer or no chlorine substituents. Accordingly, the production of hydrofluorocarbons, or compounds containing only carbon, hydrogen, and fluorine, has been the subject of increasing interest to provide environmentally desirable products for use as solvents, blowing agents, refrigerants, cleaning agents, aerosol propellants, heat transfer media, dielectrics, fire extinguishing compositions and power cycle working fluids.

In this regard, E-1-chloro-3,3,3-trifluoropropene (HCFO-1233zd(E)) is a compound that has the potential to be used as a zero Ozone Depletion Potential (ODP) and a low Global Warming Potential (GWP) refrigerant, blowing agent, aerosol propellant, solvent, etc., and as a fluorinated monomer.

SUMMARY

The present disclosure provides a method for conversion of a mixture of high-boiling fluorinated components to 1-chloro-3,3,3-trifluoropropene (HCFO-1233zd). The mixture of high-boiling fluorinated components may comprise 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), 3-chloro-1,1,1,3-tetrafluoropropane (HCFC-244fa), their isomers, and combinations thereof. Heavy impurities, such as oligomers and other high boiling impurities, such as hexachloroethane, that are present may be purged during the process to prevent yield loss and reduction of catalyst efficacy.

BRIEF DESCRIPTION OF THE DRAWING

The above mentioned and other features of the disclosure, and the manner of attaining them, will become more apparent and the disclosure itself will be better understood by reference to the following description of embodiments of the disclosure taken in conjunction with the accompanying drawing.

FIG. 1 shows a schematic of a process to synthesize 1-chloro-3,3,3-trifluoropropene (HCFO-1233zd) from a mixture of high-boiling fluorinated components.

Corresponding reference characters indicate corresponding parts throughout the several views. Although the drawing represents embodiments of various features and components according to the present disclosure, the drawing is not necessarily to scale and certain features may be exaggerated to better illustrate and explain the present disclosure. The exemplification set out herein illustrates an embodiment of the disclosure, and such exemplification is not to be construed as limiting the scope of the disclosure in any manner.

DETAILED DESCRIPTION

The present disclosure provides a process for making 1-chloro-3,3,3-trifluoropropene (HCFO-1233zd) from a mixture of high-boiling fluorinated components. Specifically, the present disclosure provides a method for manufacturing 1-chloro-3,3,3-trifluoropropene (HCFO-1233zd) from high-boiling fluorinated components produced as byproducts from a process in which 1-chloro-3,3,3-trifluoropropene (HCFO-1233zd) is produced from 1,1,1,3,3-pentachloropropene (HCC-240fa). The combined stream of byproducts may be simultaneously converted to 1-chloro-3,3,3-trifluoropropene (HCFO-1233zd).

1-Chloro-3,3,3-trifluoropropene (HCFO-1233zd) may be produced industrially by the reaction shown below in Equation 1.

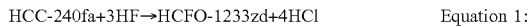
HCC-240fa+3HF→HCFO-1233zd+4HCl         Equation 1:

In this process, 1-chloro-3,3,3-trifluoropropene (HCFO-1233zd) may be produced in a liquid phase reaction without the need for a catalyst. Briefly, anhydrous hydrogen fluoride (HF) may be mixed with 1,1,1,3,3-pentachloropropene (HCC-240fa) at elevated temperature and pressure to produce the desired 1-chloro-3,3,3-trifluoropropene (HCFO-1233zd) in a mixture of E- and Z-isomers.

In the course of the reaction, partially fluorinated byproducts such as 1,1,3,3-tetrachloro-1-fluoropropane (HCFC-241fa), 1,3,3-trichloro-1,1-difluoropropane (HCFC-242fa), 3,3-dichloro-1,1,1-trifluoropropane (HCFC-243fa), and 3-chloro-1,1,1,3-tetrafluoropropane (HCFC-244fa), along with their other isomers, may be produced according to Equations 2-5, shown below.

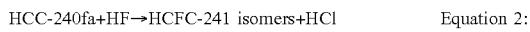
HCC-240fa+HF→HCFC-241 isomers+HCl         Equation 2:

HCC-240fa+2HF+HCFC-242 isomers+2HCl         Equation 3:

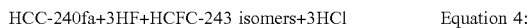
HCC-240fa+3HF+HCFC-243 isomers+3HCl         Equation 4:

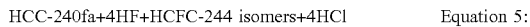
HCC-240fa+4HF+HCFC-244 isomers+4HCl         Equation 5:

The mixture of high-boiling fluorinated components may be defined as a mixture of fluorinated components with boiling points higher than 39° C.; in other words, boiling points higher than that of Z-1-chloro-3,3,3-trifluoropropene (HCFO-1233zd(Z)). The high-boiling fluorinated components may include compounds that may be converted to 1-chloro-3,3,3-trifluoropropene (HCFO-1233zd) using the methods described herein. Suitable such components may include 1,1,3,3-tetrachloro-1-fluoropropane (HCFC-241fa), 1,3,3-trichloro-1,1-difluoropropane (HCFC-242fa), 3,3-dichloro-1,1,1-trifluoropropane (HCFC-243fa), and 3-chloro-1,1,1,3-tetrafluoropropane (HCFC-244fa), along with their other isomers. For example, another isomer of HCFC-242 is 1,1,3-trichloro-1,3-difluoropropane (HCFC-242fb), and another isomer of HCFC-243 is 1,3-dichloro-1,1,3-trifluoropropane (HCFC-243fb).

Other byproducts that may be present in the feed stream or reactor stream include oligomers. Oligomers, as used herein, may be defined as dimers, trimers, tetramers, and other groups of repeated and/or mixed monomeric units that may not be easily converted to 1-chloro-3,3,3-trifluoropropene (HCFO-1233zd) using the methods described herein.

Other impurities that may also be present in the reactor as byproducts include very high boiling impurities; in other words, impurities with boiling points of greater than about 140° C. These very high boiling impurities may include CC-110 (hexachloroethane), HCO-1230 (tetrachloropropene) isomers, and some oligomers. One example of HCO-1230 isomers may be HCO-1230za (1,1,3,3-tetrachloropropene). Possible examples of oligomers may be dimers of 1,3,3-trichloro-3-fluoropropene (HCFO-1231zd) and 1,3-dichloro-3,3-difluoropropene (HCFO-1232zd), with the chemical formula $C_6H_3F_3Cl_4$. For the purpose of this invention, these very high boiling impurities, including CC-110, HCO-1230, and oligomers, may also be referred to as heavy impurities.

The present disclosure provides a method of maximizing the production of 1-chloro-3,3,3-trifluoropropene (HCFO-1233zd) by reacting a mixture of high-boiling fluorinated components with HF in the presence of a catalyst to produce 1-chloro-3,3,3-trifluoropropene (HCFO-1233zd), and removing undesired heavy impurities.

Briefly, the reactor products from Equation 1 are first separated to recover and recycle excess HF and to remove and recover the hydrogen chloride (HCl). The remaining mixture comprises E- and Z-isomers of 1-chloro-3,3,3-trifluoropropene (HCFO-1233zd); high-boiling fluorinated components; low boiling impurities such as 1,1,1,3,3-pentafluoropropane (HFC-245fa), trifluoropropyne, and E- and Z-isomers of 1,3,3,3-tetrafluoropropene (HFO-1234ze), among others; and a small amount of residual HF (usually 2 wt. % or less). This mixture may be subjected to a distillation to remove the high-boiling fluorinated components from the 1-chloro-3,3,3-trifluoropropene (HCFO-1233zd), low boiling impurities, and HF.

Following distillation, the vapor phase high-boiling fluorinated components may be passed through another reactor together with HF. The reactor may include a catalyst. Without wishing to be bound by theory, it is possible that the presence of heavy impurities in the reactor may reduce catalyst activity. Therefore, prior to entering the reactor, undesired heavy impurities may be purged. Following the reaction, any heavy impurities created may be purged prior to purification of the desired product.

An example of the process is shown in FIG. 1 and summarized below. As shown therein, a stream 12 of the high-boiling fluorinated components and heavy impurities recovered from the reaction of 1,1,1,3,3-pentachloropropene (HCC-240fa) and anhydrous HF (not shown) stored in high boiler tank 10 may be combined with a stream 16 comprising HF from an HF feed supply source, 14. The combined stream 18 may be passed to a vaporizer 20. Following vaporization, heavy impurities 22 may be passed to heavy impurity storage tank 24 for later disposal, while stream 26 comprising the high-boiling fluorinated components and HF may be passed to a reactor 30. A heating system 36 may be used to cool 32 or heat 34 the reactor 30. Reactor 30 is a gas phase reactor in which the contents of stream 26 are reacted in the gas phase, per the conditions set forth below. From reactor 30, a crude product stream 38 comprising E- and Z-isomers of 1-chloro-3,3,3-trifluoropropene (HCFO-1233zd), HF, HCl, and the newly formed heavy impurities may be passed to a partial condenser 40. At least a portion of heavy impurities 42 may be removed from partial condenser 40 and passed to heavy impurity storage tank 24. A product stream 44 comprising E- and Z-isomers of 1-chloro-3,3,3-trifluoropropene (HCFO-1233zd) may be combined with a second stream 46 comprising E- and Z-isomers of 1-chloro-3,3,3-trifluoropropene (HCFO-1233zd) from the reaction of 1,1,1,3,3-pentachloropropene (HCC-240fa) and HF (not shown) and passed as a combined stream 48 to a distillation column 50. The bottoms product 52 may be recycled back to high boiler tank 10. The overhead stream 54 comprising mostly E-1-chloro-3,3,3-trifluoropropene (HCFO-1233zd(E)) may be sent to purification columns (not shown in FIG. 1) to isolate and recover purified E-1-chloro-3,3,3-trifluoropropene (HCFO-1233zd(E)) product and recyclable by-products comprising Z-1-chloro-3,3,3-trifluoropropene (HCFO-1233zd(Z)) and 3-chloro-1,1,1,3-tetrafluoropropane (HCFC-244fa) which can be further converted to E-1-chloro-3,3,3-trifluoropropene (HCFO-1233zd(E)).

The hydrogen fluoride (HF) feed may be anhydrous. In other words, the hydrogen fluoride (HF) feed may be substantially free of water. The amount of water present in the hydrogen fluoride (HF) feed may be about 1000 ppm or less, about 750 ppm or less, about 500 ppm or less, about 250 ppm or less, about 100 ppm or less, about 50 ppm or less, about 25 ppm or less, about 10 ppm or less, about 5 ppm or less, or about 1 ppm or less.

The temperature of the outlet of vaporizer/superheater 20 may be controlled to be about 200° C. or higher, about 220° C. or higher, about 250° C. or higher, about 300° C. or higher, about 350° C. or higher, or about 400° C. or higher, or within any range of the foregoing values as endpoints.

The reaction in reactor 30 may be conducted in any suitable reaction vessel or reactor, but it should preferably be constructed from materials which are resistant to the corrosive effects of hydrogen fluoride such as nickel and its alloys, including Hastelloy, Inconel, Incoloy, and Monel. These may be single pipe or multiple tubes packed with a solid catalyst. Suitable reactors may include a catalytic pipe reactor, for example.

The temperature in reactor 30 may be about 200° C. or higher, about 210° C. or higher, about 220° C. or higher, about 230° C. or higher, about 240° C. or higher, about 250° C. or lower, about 260° C. or lower, about 270° C. or lower, about 280° C. or lower, about 290° C. or lower, about 300° C. or lower, about 310° C. or lower, about 325° C. or lower, about 350° C. or lower, about 400° C. or lower, or any value or range encompassed by these endpoints.

The pressure in reactor 30 may be maintained at about 2 psig or greater, about 5 psig or greater, about 10 psig or greater, about 15 psig or greater, about 20 psig or greater, about 25 psig or less, about 30 psig or less, about 35 psig or less, about 40 psig or less, about 45 psig or less, about 50 psig or less, about 75 psig or less, about 100 psig or less, or any value or range encompassed by these endpoints.

The molar ratio of HF/(HCFC-241 isomers+HCFC-242 isomers) may be about 0.5/1 or higher, about 0.7/1 or higher, about 0.9/1 or higher, about 1.0/1 or higher, about 1.1/1 or higher, about 1.3/1 or higher, about 1.5/1 or higher, about 2.0/1 or less, about 2.5/1 or less, about 3.0/1 or less, about 3.5/1 or less, about 4.0/1 or less, about 5.0/1 or less, or any value or range encompassed by these endpoints.

Suitable catalysts may include chromium oxides, chromium oxyfluorides, and chromium halides. The chromium oxides may include amorphous chromium oxide ($Cr_2O_3$), crystalline chromium oxide, and combinations of the foregoing. The chromium oxyfluorides may include fresh amorphous chromium oxide ($Cr_2O_3$) pretreated with HF, fresh crystalline chromium oxide ($Cr_2O_3$) pretreated with HF, amorphous chromium oxyfluoride ($CrO_xF_y$, where x may be greater than 0 but less than 1.5, and y may be greater than 0 but less than 3), crystalline chromium oxyfluoride ($CrO_xF_y$, where x may be greater than 0 but less than 1.5, and y may be greater than 0 but less than 3), and combinations of the foregoing. In one embodiment, the catalyst is amorphous chromium oxyfluoride ($CrO_xF_y$, where x may be greater than 0 but less than 1.5, and y may be greater than 0 but less than 3). The chromium halides may include chromium trifluoride ($CrF_3$), chromium trichloride ($CrCl_3$), chromium triiodide ($CrI_3$) and chromium tribromide ($CrBr_3$), and combinations of the foregoing. In one embodiment, the catalyst is chromium trifluoride ($CrF_3$).

Other suitable catalysts include promoted chromium-based catalysts, which are based on chromium and include an amount of at least one co-catalyst selected from Ni, Zn, Co, Mn, Mg, or mixtures thereof. The amount of the co-catalyst may be between 0.1 wt. % and 20 wt. % based on the total weight of the catalyst and, more particularly, may be present in an amount as little as 0.1 wt. %, 0.5 wt. %, 1.0 wt. % 1.5 wt. % or as high as 2.0 wt. %, 3.0 wt. %, 4.0 wt. %, 5.0 wt. %, 6.0 wt. %, or within any range using any two of the foregoing values as endpoints, based on to total weight of the catalyst. One suitable promoted chromium catalyst is a zinc/chromia catalyst which is based on chromia and includes an amount of zinc as a co-catalyst, for example, JM 62-3M catalyst available from Johnson Matthey. Prior to use, a fluorination treatment of the catalyst may be conducted using anhydrous HF under conditions effective to convert a portion of metal oxides into corresponding metal fluorides.

The above chromium-based catalysts may also be low chromium (VI) catalysts, having a total content of chromium (VI) oxide in an amount of about 5,000 ppm or less, about 2,000 ppm or less, about 1,000 ppm or less, about 500 ppm or less, about 250 ppm or less, or about 100 ppm or less based on total chromium oxides in the chromium oxide catalyst.

In addition to chromium-based catalysts, other suitable catalysts include alumina, iron oxide, magnesium oxide, zinc oxide, nickel oxide, cobalt oxide, aluminum fluoride or metal fluorides such as iron fluoride, magnesium fluoride, zinc fluoride, nickel fluoride, cobalt fluoride, fluorinated alumina, fluorinated iron oxide, fluorinated magnesium oxide, fluorinated nickel oxide, fluorinated cobalt oxide, titanium fluorides, molybdenum fluorides, aluminum oxyfluorides, and combinations of the foregoing. Prior to use, a fluorination treatment of catalyst containing metal oxide(s) is conducted using anhydrous HF under conditions effective to convert a portion of metal oxide(s) into corresponding metal fluoride(s).

The heating system may comprise any suitable heating medium capable of achieving and/or maintaining the temperatures required by the process. Suitable heating media may include molten salt, hot oil, high pressure steam, and electric heaters (resistance or induction), among others, for example.

The partial condenser 40 may be operated at a temperature of about 10° C. or higher, about 20° C. or higher, about 30° C. or higher, about 40° C. or higher, about 50° C. or less, about 60° C. or less, about 70° C. or less, about 80° C. or less, or any value or range encompassed by these endpoints.

The partial condenser 40 may be operated at a pressure of about 1 bar or greater, about 2 bar or greater, about 3 bar or less, about 4 bar or less, about 5 bar or less, or any value or range encompassed by these endpoints.

The distillation column 50 may be operated at a top distillate temperature of about 10° C. or greater, about 20° C. or greater, about 30° C. or greater, about 40° C. or less, about 50° C. or less, about 60° C. or less, or any value or range encompassed by these endpoints.

The distillation column 50 may be operated at a pressure of about 1 bar or greater, about 2 bar or greater, about 3 bar or less, about 4 bar or less, about 5 bar or less, or any value or range encompassed by these endpoints.

The heavy impurities in the storage tank may be purged. Alternatively, the heavy impurities in the storage tank may be treated, for example by distillation such as distillation under vacuum, to recover useful components such as 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), and 3-chloro-1,1,1,3-tetrafluoropropane (HCFC-244fa), and their isomers, for example, which can be sent to the reactor for conversion to 1-chloro-3,3,3-trifluoropropene (HCFO-1233zd) product, as well as other useful components such as 1,1,3,3-tetrachloropropene (HCO-1230za) and its isomers, which can be sent to 240fa reactor for conversion to 1-chloro-3,3,3-trifluoropropene (HCFO-1233zd) product.

The lights products produced during the process may comprise E-1,3,3,3-tetrafluoropropene (HFO-1234ze(E)), Z-1,3,3,3-tetrafluoropropene (HFO-1234ze(Z)), and 1,1,3,3-pentafluoropropane (HFC-245fa). Other products produced during the process may comprise 2-chloro-3,3,3-trifluoropropene (HCFO-1233xf); isomers of HCFO-1232, HCFO-1231, and HFO-1230; 1-chloro-1,3,3,3-tetrafluoropropane (HCFC-244fa), trichloropropene isomers, hexachloroethane, dimers such as $C_6H_4F_8$ isomers, $C_6H_3F_7$ isomers, $C_6H_4F_7Cl$ isomers, $C_6H_3F_6Cl$ isomers, and $C_6H_3F_3Cl_4$ isomers, among others.

The percent conversion of 1,1,3,3-tetrachloro-1-fluoropropane (HCFC-241fa) to 1-chloro-3,3,3-trifluoropropene (HCFO-1233zd) may be about 70% or greater, about 80% or greater, about 90% or greater, about 91% or greater, about 92% or greater, about 93% or greater, about 95% or greater, about 96% or greater, about 97% or greater, about 98% or greater, or about 99% or greater.

The percent conversion of HCFC-242 isomers (non-limiting examples include 1,3,3-trichloro-1,1-difluoropropane (HCFC-242fa) and 1,1,3-trichloro-1,3-difluoropropane (HCFC-242fb)) to 1-chloro-3,3,3-trifluoropropene (HCFO-1233zd) may be about 50% or greater, about 60% or greater, about 70% or greater, about 80% or greater, about 90% or greater, about 91% or greater, about 92% or greater, about 93% or greater, about 95% or greater, about 96% or greater, about 97% or greater, about 98% or greater, about 99% or greater, or about 99.5% or greater.

The percent conversion of HCFC-243 isomers (non-limiting examples include 3,3-dichloro-1,1,1-trifluoropropane (HCFC-243fa) and 1,3-dichloro-1,1,3-trifluoropropane (HCFC-243fb)) to 1-chloro-3,3,3-trifluoropropene (HCFO-1233zd) may be about 20% or greater, about 30% or greater, about 40% or greater, about 45% or greater, about 50% or greater, about 55% or greater, about 60% or greater, about 70% or greater, about 80% or greater, or about 90% or greater.

The percent conversion of 3-chloro-1,1,1-3-tetrafluoropropane (HCFC-244fa) to 1-chloro-3,3,3-trifluoropropene (HCFO-1233zd) may be about 20% or greater, about 30% or greater, about 40% or greater, about 50% or greater, about 60% or greater, about 70% or greater, about 80% or greater, or about 90% or greater.

The total selectivity for E- and Z-isomers of 1-chloro-3,3,3-trifluoropropene (HCFO-1233zd) may be about 70% or greater, about 75% or greater, about 80% or greater, about 85% or greater, about 90% or greater, about 95% or greater, or about 99% or greater. While E-1-chloro-3,3,3-trifluoropropene HCFO-1233zd(E)) may be separated and purified as a product, Z-1-chloro-3,3,3-trifluoropropene HCFO-1233zd (Z)) may be separated/recovered and fed to an isomerization reactor to be converted to E-1-chloro-3,3,3-trifluoropropene HCFO-1233zd(E)).

EXAMPLES

Example 1

Conversion of Fluorinated Compounds to 1233zd

A stream comprising HCFO-1233zd(E) (68.75%), HCFO-1233zd(Z) (4.08%), HCl (0.05%), HF (1.66%), HCFC-241 isomers (5.40%), HCFC-242 isomers (15.98%), HCFC-243 isomers (1.60%), HCFC-244 isomers (0.68%), HFC-245 isomers (0.12%), HCFO-1232zd (0.03%), HFO-1234ze(Z) (1.26%), HFO-1234ze(E) (0.19%), CC-110 (0.02%) and oligomers (0.19%) is subjected to separation by distillation and phase separation of immiscible liquids to remove HCl, HF and HCC-240fa, as well as other underfluorinated intermediates such as HCFC-241fa, which are recycled to the reactor. The remaining mixture comprising the components described above are distilled to remove the higher boiling products as a bottom stream. HCFO-1233zd (E) and HCFO-1233zd(Z) are recovered in the top distillate from this distillation to provide a crude product stream. The crude product stream is then subjected to further purification, including caustic scrubbing, water removal, distillation, and conversion of the HCFO-1233zd(Z) to HCFO-1233zd(E). These purification steps produce HCFO-1233zd (E) in the desired purity.

The bottom stream comprising the higher boiling products is collected in a vessel, such as a High Boiler Tank, then fed by gravity to a vaporizer and superheater together with anhydrous HF to produce a vapor stream comprising HF (10.26%), HCFC-241 isomers (19.8%), HCFC-242 isomers (60.37%), HCFC-243 isomers (8.02%), HCFC-244 isomers (0.004%), HCFO-1232zd (0.28%), HCFO-1233zd(Z) (0.018%), and heavy impurities (1.248%). In this example, the vapor stream is heated to 220° C.

A liquid purge comprising HF (0.15%), HCFC-241 isomers (27.98%), HCFC-242 isomers (33.39%), HCFC-243 isomers (1.84%), HCFO-1232zd (0.06%) and heavy impurities (36.58%) is removed from the vaporizer to remove heavy impurities that can negatively affect the catalyst. The vapor stream then enters the reactor where additional HCFO-1233zd is produced by the reaction of the high boiling fluorinated compounds and HF. The reactor product stream comprising HCFO-1233zd(E) (51.23%), HCFO-1233zd(Z) (0.4%), HCl (32.75%), HF (0.91%), HCFC-241 isomers (0.22%), HCFC-242 isomers (3.02%), HCFC-243 isomers (2.85%), HCFC-244 isomers (0.47%), HFC-245 isomers (1.07%), HCFO-1232zd (0.24%), HFO-1234ze(E) (1.00%), HFO-1234ze(Z) (0.25%), and heavy impurities (5.59%) is partially condensed to remove a stream comprising new heavy impurities formed in the reaction and heavy impurities that may not have been removed in the purge stream upstream of the reactor. The combined heavy impurities from these two streams may be disposed by suitable methods, such as incineration, or may be subjected to further purification, such as vacuum, atmospheric, or super-atmospheric distillation to recover additional useful high boiling fluorinated compounds to recycle for further conversion in this reactor.

A product stream from the partial condenser comprising HCFO-1233zd(E) (54.22%), (HCFO-1233zd(Z) (0.41%), HCFC-241 isomers (0.05%), HCFC-242 isomers (1.61%), HCFC-243 isomers (2.33%), HCFC-244 isomers (0.46%), HFC-245 isomers (1.15%), HCFO-1232zd (0.21%), HFO-1234ze(E) (1.10%), HFO-1234ze(Z) (0.27%), and heavy impurities (0.93%), unconverted HF (1.0%), and HCl (36.26%) is passed to a distillation column where the unconverted high boiling fluorinated compounds are removed and recycled in the bottom stream, and the unconverted HF and the HCFO-1233zd and HCl products are removed in the overhead stream.

Example 2

Conversion of High-Boiling Fluorinated Components to 1233zd with Fluorinated $Cr_2O_3$ Catalyst A single pass unit was used for the reaction. The unit consisted of a feed delivery system, vaporizer, reactor, pressure control RCV, caustic solution scrubber, drying column, and PCC (product collection cylinder). A 2" Inconel 600 pipe reactor was used. The reactor was immersed in a sand bath for heating. A 5-point thermocouple was placed in the middle of catalyst bed to measure process temperatures. The distance between two adjacent probe points was five inches between the first two points, and four inches thereafter.

One liter of fluorinated chromia (aka chromium oxyfluoride) catalyst was loaded into the reactor. The reactor was heated to the desired temperature under nitrogen. After the temperature was stabilized, organic and HF flows were fed into two steam vaporizers in series for vaporization, and the vaporized feed stream was fed to the bottom of catalyst bed to start the reaction. The reactor effluent was sent to caustic solution scrubber for acid removal and then to a drying column containing Drierite before being collected in a chilled PCC. During operation, samples were periodically taken from the reactor outlet into DI water-loaded gas bags for GC and GC-MS analyses. Before the GC or GC-MS analysis of the liquid organic layer, the reactor effluent sample was chilled 30 minutes prior to adding dichloromethane (DCM) to the bag and chilling for a further 30 minutes.

The composition of the organic feed for the reaction is shown below in Table 1.

TABLE 1

| Component | GC area % |
|---|---|
| HCFC-244fa | 1.2107 |
| HCFO-1233zd(Z) | 4.7336 |
| HCFC-243fa | 0.3250 |
| HCFC-243fb | 6.6738 |

TABLE 1-continued

| Component | GC area % |
|---|---|
| HCFC-242fa | 66.4196 |
| HCFC-242fb | 3.0694 |
| HCFC-241fa | 16.0273 |
| Others | 1.5406 |

As seen therein, the sum of HCFC-241, HCFC-242, and HCFC-243 isomers was over 92% of the total organic composition.

The reaction was carried out using a fresh chromia catalyst. The other reaction conditions, averaged over the 266 hours, are shown in Table 2.

TABLE 2

| Time on stream h | Feed rates | | Reactor pressure psig | Sand bath Temp. °C | Catalyst bed temperatures °C | | | | |
|---|---|---|---|---|---|---|---|---|---|
| | Organic lb/h | HF g/h | | | Inlet A | B | C | D | E |
| 266 | 0.56 | 30 | 10.6 | 220 | 213.8 | 216.0 | 217.7 | 217.1 | 217.6 |

As shown in Table 2, the temperatures of catalyst bed were slightly lower than the sand bath temperature, indicating that the reaction was slightly endothermic in nature.

The conversions of HCFC-241, HCFC-242, and HCFC-243, along with the selectivities of lights, HCFO-1233zd(E), HCFO-1233zd(Z), and others over the 266-hour reaction time are shown in Table 3. Lights comprised E-1,3,3,3-tetrafluoropropene (HFO-1234ze(E)), Z-1,3,3,3-tetrafluoropropene (HFO-1234ze(Z)), and 1,1,3,3-pentafluoropropane (HFC-245fa). Others comprised 2-chloro-3,3,3-trifluoropropene (HCFO-1233xf); isomers of HCFO-1232, HCFO-1231, and HCO-1230; 1-chloro-1,3,3,3-tetrafluoropropane (HCFC-244fa), trichloropropene isomers, hexachloroethane, dimers such as $C_6H_4F_8$ isomers, $C_6H_3F_7$ isomers, $C_6H_4F_7Cl$ isomers, $C_6H_3F_6Cl$ isomers, $C_6H_3F_3Cl_4$ isomers, and unknowns.

TABLE 3

| PCC wt. gain lb/h | Conversion, % | | | | Product selectivity, % | | | HCFO-1233zdE productivity, lbs/h/ft³ |
|---|---|---|---|---|---|---|---|---|
| | HCFC-243 | HCFC-242 | HCFC-241 | Lights | HCFO-1233zd(E) | HCFO-1233zd(Z) | Others | |
| 0.30 | 47.31 | 95.78 | 99.54 | 1.82 | 89.56 | 1.04 | 7.58 | 8.6 |

As shown in Table 3, the selectivity for and production of HCFO-1233zd(E) were about 90% and 8.6 lbs/h/ft³, respectively. A reactor effluent sample was taken after 219 hours on stream for GO-MS analysis and the results are presented in Table 4.

TABLE 4

| Peak # | RT (min) | Component Name | Area % - FID |
|---|---|---|---|
| 1 | 12.878 | HFO-1234ze (E) | 0.117 |
| 2 | 14.947 | HFC-245fa | 0.670 |
| 3 | 16.132 | HFO-1234ze (Z) | 0.023 |
| 4 | 18.642 | HCFO-1233xf | 0.033 |
| 5 | 19.517 | HCFO-1233zd (E) | 68.884 |
| 6 | 20.288 | HCFC-244fa | 0.814 |
| 7 | 21.256 | HCFO-1233zd (Z) | 6.628 |
| 8 | 21.68 | HFO—$C_6H_4F_8$ isomer | 0.006 |
| 9 | 21.811 | HFO—$C_6H_3F_7$ isomer | 0.008 |
| 10 | 22.093 | Methylene chloride[1] | 3.734 |
| 11 | 22.62 | HCFO-1223xd | 0.010 |
| 12 | 22.911 | HCFO-1232 isomer | 0.008 |
| 13 | 23.09 | HCFO-1232 isomer | 1.506 |
| 14 | 23.306 | HCFC-243fa | 4.441 |
| 15 | 23.429 | HCFC-243fb | 0.317 |
| 16 | 23.918 | HCFO-1232 isomer | 0.027 |
| 17 | 23.974 | HCFO-$C_6H_4F_7Cl$ isomer | 0.023 |
| 18 | 24.087 | unknown | 0.004 |
| 19 | 24.143 | HCFO-$C_6H_3F_6Cl$ isomer | 0.020 |
| 20 | 24.228 | HCFC-242fa | 0.425 |
| 21 | 25.121 | HCFO-$C_6H_3F_6Cl$ isomer | 0.021 |
| 22 | 25.723 | HCFC-242fb | 4.418 |
| 23 | 25.911 | HCFO-1231 isomer | 0.120 |
| 24 | 25.986 | HCFO-1231 isomer | 0.071 |
| 25 | 26.221 | HCFC-242 isomer | 0.040 |
| 26 | 26.466 | HCO-$C_4H_6C_{l2}$ isomer | 0.247 |
| 27 | 26.814 | HCFO-1231 isomer | 0.006 |
| 28 | 27.105 | CO-Perchloroethylene | 0.010 |
| 29 | 27.237 | HCO-trichloropropene isomer | 0.010 |
| 30 | 27.66 | HCO-trichloropropene isomer | 0.006 |
| 31 | 28.328 | HCFC-241 fa | 0.009 |
| 32 | 28.657 | CFC-111 | 0.011 |
| 33 | 28.647 | HCO-tetrachloropropene isomer | 0.037 |
| 34 | 29.005 | HCO-tetrachloropropene isomer | 7.035 |
| 35 | 30.152 | HCO-tetrachloropropene isomer | 0.063 |
| 36 | 31.525 | HCC-240fa | 0.002 |
| 37 | 31.628 | HCFO-$C_6H_3F_3Cl_4$ isomer | 0.008 |
| 38 | 32.202 | HCO-pentachloropropene isomer | 0.012 |

TABLE 4-continued

| Peak # | RT (min) | Component Name | Area % - FID |
|---|---|---|---|
| 39 | 32.455 | CC-110 | 0.102 |
| 40 | 32.578 | HCFO-$C_6H_3F_3Cl_4$ isomer | 0.035 |
| 41 | 32.813 | HCFO-$C_6H_3F_3Cl_4$ isomer | 0.008 |
| 42 | 33.189 | HCFO-$C_6H_3F_3Cl_4$ isomer | 0.018 |

[1]Externally added for analysis purposes

HCFO-1233zd(E) was formed as a major component in 68.884%. Light components such as HFO-1234ze(E), HFC-245fa, and HFO-1234zeZ and a number of other components such as HCFO-1233xf, HCFO-1232 isomers, HCFO-1231 isomers, HCO-1230 isomers, HCFC-244fa, trichloropropene isomers, hexachloroethane, dimers such as $C_6H_4F_8$ isomers, $C_6H_3F_7$ isomers, $C_6H_4F_7Cl$ isomers, $C_6H_3F_6Cl$ isomers, $C_6H_3F_3Cl_4$ isomers, and unknowns were also formed as byproducts.

Examples 3-27

Conversion of High-Boiling Fluorinated Components to 1233zd with Other Catalysts Example 2 above is repeated except that, instead of fluorinated $Cr_2O_3$ catalyst, other catalysts are used. Similar results are obtained as to yield and selectivity for producing E-1-chloro-3,3,3-trifluoropropene (HCFO-1233zd(E)).

TABLE 5

Other catalysts used

| Example | Catalyst |
|---|---|
| 3 | Chromium trifluoride (CrF3) |
| 4 | Chromium trichloride ($CrCl_3$) |
| 5 | Chromium triiodide ($CrI_3$) |
| 6 | Chromium tribromide ($CrBr_3$) |
| 7 | Chromium/zinc with 2.3 wt. % Zn |
| 8 | Chromium oxide with less than 500 ppm chromium (VI) oxide |
| 9 | Alumina |
| 10 | Iron oxide |
| 11 | Magnesium oxide |
| 12 | Zinc oxide |
| 13 | Nickel oxide |
| 14 | Cobalt oxide |
| 15 | Zinc fluoride |
| 16 | Magnesium fluoride |
| 17 | Nickel fluoride |
| 18 | Titanium fluoride |
| 19 | Molybdenum fluoride |
| 20 | Cobalt fluoride |
| 21 | Aluminum fluoride |
| 22 | Aluminum oxyfluoride |
| 23 | Iron fluoride |
| 24 | Fluorinated magnesium oxide |
| 25 | Fluorinated nickel oxide |
| 26 | Fluorinated cobalt oxide |
| 27 | Fluorinated iron oxide |

Example 28

Purging of Heavy Impurities

The process of FIG. 1 is carried out with heavy impurities purged from vaporizer 20 via stream 22, followed by reaction of the vaporized stream 26 according the Examples 1 and 2 above.

The process of FIG. 1 is carried out again with heavy impurities purged from condenser 40 via stream 42 following reaction of the vaporized stream 26 according the Examples 1 and 2 above.

The process of FIG. 1 is carried out with heavy impurities purged both from vaporizer 20 via stream 22, followed by reaction of the vaporized stream 26 according the Examples 1 and 2 above, as well as with heavy impurities purged from condenser 40 via stream 42 following reaction of the vaporized stream 26 according the Examples 1 and 2 above.

Aspects

Aspect 1 is a method for conversion of a mixture of high-boiling fluorinated components to 1-chloro-3,3,3-trifluoropropene (HCFO-1233zd), comprising: contacting the mixture with hydrogen fluoride (HF) to produce a combined reactant stream; vaporizing the combined reactant stream to produce vaporized reactant stream; reacting the vaporized reactant stream in the presence of a catalyst to produce a product stream comprising E-1-chloro-3,3,3-trifluoropropene (HCFO-1233zd(E)) and heavy impurities; condensing at least a portion of heavy impurities; and optionally purifying the product stream to produce E-1-chloro-3,3,3-trifluoropropene (HCFO-1233zd(E)).

Aspect 2 is the method of Aspect 1, wherein the high-boiling fluorinated components have a boiling point of greater than 39° C.

Aspect 3 is the method of either Aspect 1 or Aspect 2, wherein the mixture of high-boiling fluorinated components comprises 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), 3-chloro-1,1,1,3-tetrafluoropropane (HCFC-244fa), and combinations thereof.

Aspect 4 is the method of any one of Aspects 1 to 3, wherein the vaporization step is conducted at a temperature of 220° C. or higher.

Aspect 5 is the method of any one of Aspects 1 to 4, wherein the reacting step is conducted at a temperature between 200° C. and 300° C.

Aspect 6 is the method of any one of Aspects 1 to 5, wherein the condensing step is conducted at a temperature of 10° C. or higher.

Aspect 7 is the method of any one of Aspects 1 to 6, wherein the catalyst is selected from the group consisting of chromium oxides, chromium oxyfluorides, and chromium halides.

Aspect 8 is the method of any one of Aspects 1 to 7, wherein the catalyst is a chromium oxyfluoride catalyst.

Aspect 9 is the method of any one of Aspects 1 to 8, wherein the composition further comprises heavy impurities with a boiling point of greater than 140° C.

Aspect 10 is the method of Aspect 9, wherein the heavy impurities are purged from the vaporizer.

Aspect 11 is the method of either Aspect 9 or Aspect 10, wherein the heavy impurities are purged from the partial condenser.

Aspect 12 is a method for conversion of a mixture of high-boiling fluorinated components to 1-chloro-3,3,3-trifluoropropene (HCFO-1233zd), comprising: contacting the mixture with hydrogen fluoride (HF) to produce a combined reactant stream; vaporizing the combined reactant stream to produce a vaporized reactant stream and a heavy impurity stream; separating the heavy impurity stream from the vaporized reactant stream; reacting the vaporized reactant stream in the presence of a catalyst to produce a product stream comprising E-1-chloro-3,3,3-trifluoropropene (HCFO-1233zd(E)); and optionally purifying the product stream to produce E-1-chloro-3,3,3-trifluoropropene (HCFO-1233zd(E)).

Aspect 13 is the method of Aspect 12, wherein the high-boiling fluorinated components have a boiling point of greater than 39° C.

Aspect 14 is the method of either Aspect 12 or Aspect 13, wherein the mixture of high-boiling fluorinated components comprises 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), 3-chloro-1,1,1,3-tetrafluoropropane (HCFC-244fa), and combinations thereof.

Aspect 15 is the method of any one of Aspects 12 to 14, wherein the vaporization step is conducted at a temperature of 220° C. or higher.

Aspect 16 is the method of any one of Aspects 12 to 15, wherein the reacting step is conducted at a temperature between 200° C. and 300° C.

Aspect 17 is the method of any one of Aspects 12 to 16, wherein the condensing step is conducted at a temperature of 10° C. or higher.

Aspect 18 is the method of any one of Aspects 12 to 17, wherein the catalyst is selected from the group consisting of chromium oxides, chromium oxyfluorides, and chromium halides.

Aspect 19 is the method of any one of Aspects 12 to 18, wherein the catalyst is a chromium oxyfluoride catalyst.

Aspect 20 is the method of any one of Aspects 12 to 19, wherein the heavy impurity stream comprises components having a boiling point of greater than 140° C.

Aspect 21 is the method of any of Aspects 1-11 or Aspects 12-20, wherein: the vaporization step is conducted at a temperature of 220° C. or higher; the condensing step is conducted at a temperature of 10° C. or higher; and the catalyst is chromium oxide.

Aspect 22 is the method of any of Aspects 1-11 or Aspect 12-20, wherein the catalyst is selected from alumina, iron oxide, magnesium oxide, zinc oxide, nickel oxide, cobalt oxide, aluminum fluoride, iron fluoride, magnesium fluoride, zinc fluoride, nickel fluoride, cobalt fluoride, fluorinated alumina, fluorinated iron oxide, fluorinated magnesium oxide, fluorinated nickel oxide, fluorinated cobalt oxide, titanium fluoride, molybdenum fluoride, aluminum oxyfluoride, and combinations of the foregoing.

Aspect 23 is the method of any of Aspects 1-11 or Aspect 12-20, wherein the catalyst is a zinc/chromium catalyst including 0.5 to 6.0 wt. % Zn, based on the total weight of the catalyst.

Aspect 23 is the method of any of Aspects 1-11 or Aspect 12-20, wherein the catalyst is a chromium catalyst having chromium (VI) oxide in an amount of less than 1,000 ppm, less than 500 ppm, less than 150 ppm or less than 100 ppm.

While this disclosure has been described as relative to exemplary designs, the present disclosure may be further modified within the spirit and scope of this disclosure. Further, this application is intended to cover such departures from the present disclosure as come within known or customary practice in the art to which this disclosure pertains.

The invention claimed is:

1. A method for conversion of a mixture of high-boiling fluorinated components to 1-chloro-3,3,3-trifluoropropene (HCFO-1233zd), comprising:

contacting the mixture with hydrogen fluoride (HF) to produce a combined stream, the mixture comprising heavy impurities with a boiling point of greater than 140° C.;

vaporizing the combined stream in a vaporizer to produce vaporized reactant stream;

purging the heavy impurities from the vaporizer;

reacting the vaporized reactant stream in the presence of a catalyst to produce a product stream comprising E-1-chloro-3,3,3-trifluoropropene (HCFO-1233zd(E)) and additional heavy impurities with a boiling point of greater than 140° C.;

condensing, and purging from the product stream, at least a portion of the additional heavy impurities; and optionally purifying the product stream.

2. The method of claim 1, wherein the high-boiling fluorinated components have a boiling point of greater than 39° C.

3. The method of claim 1, wherein the mixture of high-boiling fluorinated components comprises 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), 3-chloro-1,1,1,3-tetrafluoropropane (HCFC-244fa), and combinations thereof.

4. The method of claim 1, wherein the vaporization step is conducted at a temperature of 220° C. or higher.

5. The method of claim 1, wherein the reacting step is conducted at a temperature between 200° C. and 300° C.

6. The method of claim 1, wherein the condensing step is conducted at a temperature of 10° C. or higher.

7. The method of claim 1, wherein the catalyst is selected from the group consisting of chromium oxides, chromium oxyfluorides, and chromium halides.

8. The method of claim 1, wherein the catalyst is a chromium oxyfluoride catalyst.

9. The method of claim 1, wherein:

the vaporization step is conducted at a temperature of 220° C. or higher;

the condensing step is conducted at a temperature of 10° C. or higher; and the catalyst is chromium oxide.

10. The method of claim 1, wherein the catalyst is a zinc/chromium catalyst including 0.5 to 6.0 wt. % Zn, based on the total weight of the catalyst.

11. A method for conversion of a mixture of high-boiling fluorinated components to 1-chloro-3,3,3-trifluoropropene (HCFO-1233zd), comprising:

contacting the mixture with hydrogen fluoride (HF) to produce a combined stream, the mixture comprising heavy impurities with a boiling point of greater than 140° C.;

vaporizing the combined stream to produce a vaporized reactant stream and a heavy impurity stream;

separating the heavy impurity stream from the vaporized reactant stream;

reacting the vaporized reactant stream in the presence of a catalyst to produce a product stream comprising E-1-chloro-3,3,3-trifluoropropene (HCFO-1233zd(E)) and additional heavy impurities with a boiling point of greater than 140° C.;

condensing, and purging from the product stream, at least a portion of the additional heavy impurities; and optionally purifying the product stream.

12. The method of claim 11, wherein the high-boiling fluorinated components have a boiling point of greater than 39° C.

13. The method of claim 11, wherein the mixture of high-boiling fluorinated components comprises 1,1,3,3-tetrachloro-1-fluoropropane (HCFC-241fa), 1,3,3-trichloro-1,1-difluoropropane (HCFC-242fa), 1,1,3-trichloro-1,3-difluoropropane (HCFC-242fb), 3,3-dichloro-1,1,1-trifluoropropane (HCFC-243fa), 1,3-dichloro-1,1,3-trifluoropropane (HCFC-243fb), 3-chloro-1,1,1,3-tetrafluoropropane (HCFC-244fa), and combinations thereof.

14. The method of claim 11, wherein the vaporization step is conducted at a temperature of 220° C. or higher.

15. The method of claim 11, wherein the reacting step is conducted at a temperature between 200° C. and 300° C.

16. The method of claim 11, wherein the condensing step is conducted at a temperature of 10° C. or higher.

17. The method of claim 11, wherein the catalyst is selected from the group consisting of chromium oxides, chromium oxyfluorides, and chromium halides.

18. The method of claim 11, wherein the catalyst is a chromium oxyfluoride catalyst.

19. The method of claim 1, wherein the mixture of high boiling fluorinated components comprises by-products derived from reacting HCC-240fa to form HFO-1233zd.

20. The method of claim 11, wherein the mixture of high boiling fluorinated components comprises by-products derived from reacting HCC-240fa to form HFO-1233zd.

\* \* \* \* \*